United States Patent
Rossi et al.

(10) Patent No.: US 6,494,853 B1
(45) Date of Patent: Dec. 17, 2002

(54) HIP SUPPORT

(75) Inventors: Paolo Rossi, Stansstad (CH); Aldo Bernareggi, Milan (IT)

(73) Assignee: Orthoscharer & Co. di Paolo Rossi & Co., Stansstad (CH)

( * ) Notice: Subject to any disclaimer, the term of this patent is extended or adjusted under 35 U.S.C. 154(b) by 0 days.

(21) Appl. No.: 09/612,888

(22) Filed: Jul. 10, 2000

(30) Foreign Application Priority Data

Jul. 13, 1999 (IT) .......................................... MI99A1538

(51) Int. Cl.⁷ .................................................. A61F 5/00
(52) U.S. Cl. .......................................... 602/16; 602/19
(58) Field of Search ............................... 602/5, 16, 19; 128/846, 869, 882

(56) References Cited

U.S. PATENT DOCUMENTS

| | | | |
|---|---|---|---|
| 4,531,515 A | * | 7/1985 | Rolfes .......................... 602/16 |
| 4,905,678 A | | 3/1990 | Cumins |
| 5,368,552 A | | 11/1994 | Williamson |
| 5,421,810 A | | 6/1995 | Davis |
| 5,538,499 A | | 7/1996 | Schwenn |
| 5,860,943 A | | 1/1999 | Bloedau |
| 6,027,466 A | * | 2/2000 | Diefenbacher ............... 602/16 |
| 6,039,707 A | * | 3/2000 | Crawford ..................... 602/19 |
| 6,129,689 A | * | 10/2000 | Dibello ........................ 602/16 |

* cited by examiner

Primary Examiner—Michael A. Brown
(74) Attorney, Agent, or Firm—Hedman & Costigan, P.C.

(57) ABSTRACT

An improved hip support characterized by a pelvis harness connected by means of an articulated rod to a thigh harness. The pelvis harness includes a central belt connected to two containment elements of the head of a femur by means of an orientable connection, and being closable by means of closing elements. The orientable connection is made by means of at least one first plate associated to overlapping portions of the central belt and of each of the containment elements, which are clamped together by means of closing elements which can be dismantled. The first plate has rough parts in relief that penetrate inside the body of said pelvis harness so as to clamp the coupling.

14 Claims, 3 Drawing Sheets

HIP SUPPORT

The present invention refers to an improved hip support.

Hip supports are surgical medical appliances that are worn by people who have chronic problems of hip dislocation. In fact, increasingly frequently elderly people, and in particular women, undergo operation for reconstruction of the head of the femur by means of a titanium prosthesis. In the case of such subjects, in a period of variable duration following upon the surgical operation, the head of the femur needs to be blocked inside its seat in the hip to prevent it from coming out. If such an eventuality were to occur, a new surgical operation would be required, with all the difficulties and consequences that this involves for the patient.

Should precautions fail to be taken, a circumstance of this type would arise quite often and in a large number of situations. In this connection, it is sufficient to consider that even when a person stands up from a sitting position, he or she tends always to rotate slightly, and this, in people who are particularly predisposed, would cause the undesired effect of the head of the femur coming out of its seat in the hip, with the consequent need for a surgical operation.

At present, hip supports are made of a first element designed to be worn around the pelvis and referred to usually as "pelvis harness", which is connected to a second element designed to be worn on a thigh and referred to as "thigh harness". The pelvis harness and the thigh harness are made of moulded plates of plastic material, and they are connected together by means of an articulated rod that is fixed to them.

In typical traditional embodiments, the pelvis harness comprises a central belt, to the ends of which are connected elements for containing the head of the femur. To make the connection in a way that can be regulated, the central belt is provided with two sets of through holes set on top of one another, which are aligned with two holes, which are also through holes and set on top of one another, of the containment elements. Inserted in the aligned holes are screws for clamping the containment elements with respect to the central belt. In addition, the containment elements are provided with a strap for closing the pelvis harness once the latter has been put on.

In a different embodiment, the connection of the central belt of the pelvis harness to the containment elements is achieved by parts made up of rough material that is added set between the central belt and the containment elements. The said parts are pressed into contact with one another by clasps inserted in a slot of the central belt and in a hole of each containment element.

Furthermore, each containment element is connected, by means of a pair of screws, to one end of at least one articulated rod, according to the patient's needs.

The second end of the articulated rod is fixed, again by means of screws, to the thigh harness.

The thigh harness is made by means of a shell element open along one side and provided with straps for closing so that the harness embraces the patient's thigh.

The aforesaid traditional hip supports may notoriously prove uncomfortable to use and not very effective. In particular, traditional pelvis harnesses may cause considerable discomfort if worn for long periods and may prove far from reliable. In fact, for the first embodiment described for connection between the central belt and lateral containment elements, the screws used to make the connection of the central belt to the containment elements enable only adjustment in width of the pelvis harness, but not rotation of the containment elements to adapt them to the pelvis of the person wearing the hip support.

Instead, the second embodiment, albeit enabling an adjustment in width and in rotation of the containment elements, proves not very reliable. This is because the rough elements, with the passage of time, tend to wear out, thus losing their capacity to fasten the various pieces in contact, so that the latter can slide and rotate with respect to one another.

To this it should be added that the clasps press against the user's kidneys when a traditional hip support is worn, so causing even very intense pain.

In addition to being in itself an extremely tiresome drawback, this may lead the patient to assume incorrect and harmful positions.

Furthermore, since the articulated rod is fixed to the pelvis harness and to the thigh harness exclusively by means of screws and is not housed in seats that define its position, in certain cases problems may arise of positioning of the thigh harness with respect to the pelvis harness. This occurs because, for example, when the hip support is to be applied to a person of short stature, the orthopaedic technician cuts the metal rod so that the thigh harness and the pelvis harness, when assembled, are at a correct distance apart. Frequently, however, when the rod is cut, one of the seats for one of the clamping screws is removed. When this occurs, the connection between the thigh harness or pelvis harness and the rod depends upon a single screw only. For this reason, the rod inevitably tends to rotate and, in any case, does not guarantee perfect alignment between the thigh harness and the pelvis harness.

A purpose of the present invention is to eliminate the technical problems referred to above by providing an improved hip support that is substantially comfortable and does not cause distress for the patient wearing it, even after long periods of time.

Another purpose of the present invention is to provide a hip support that is always effective and reliable.

A further purpose of the present invention is to provide a hip support the elements of which can always be positioned and fitted together in an appropriate way so as to perform their function in an optimal manner all the time.

Not the least important purpose of the present invention is to provide a an improved hip support that is basically simple and safe.

These and other purposes according to the present invention are achieved by providing an improved hip support.

Other characteristics of the present invention are moreover defined in the ensuing claims.

Advantageously, the hip support according to the present invention is made of injection-moulded plastic material. This production process enables not only to make the component elements of variable thickness, thickening the portions that are subject to larger stresses and lightening the portions that are subject to less stress, but also enables safety borders in relief to be made along all the edges of the elements of the hip support. This production process moreover enables considerable containment of the costs of production of the hip support according to the invention as compared to traditional hip supports, so that it is possible to provide hip supports that are basically economical.

Further characteristics and advantages of an improved hip support according to the present invention will emerge more clearly evident from the ensuing description, which is provided purely to give an explanatory and non-limiting example, with reference to the attached schematic drawings, in which.

Figure 1:
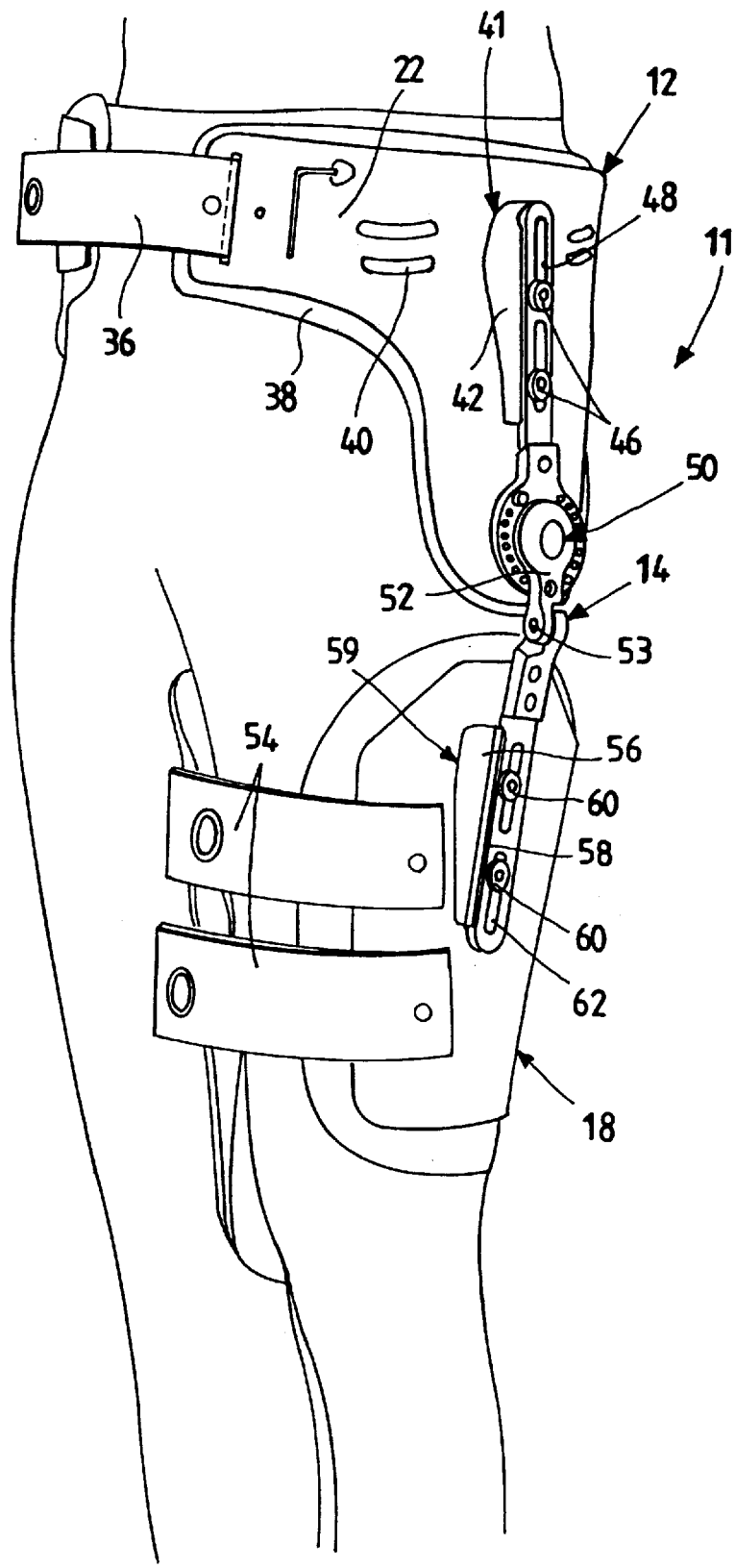
FIG. 1 is a perspective view of a hip support according to the present invention.
Figure 2:
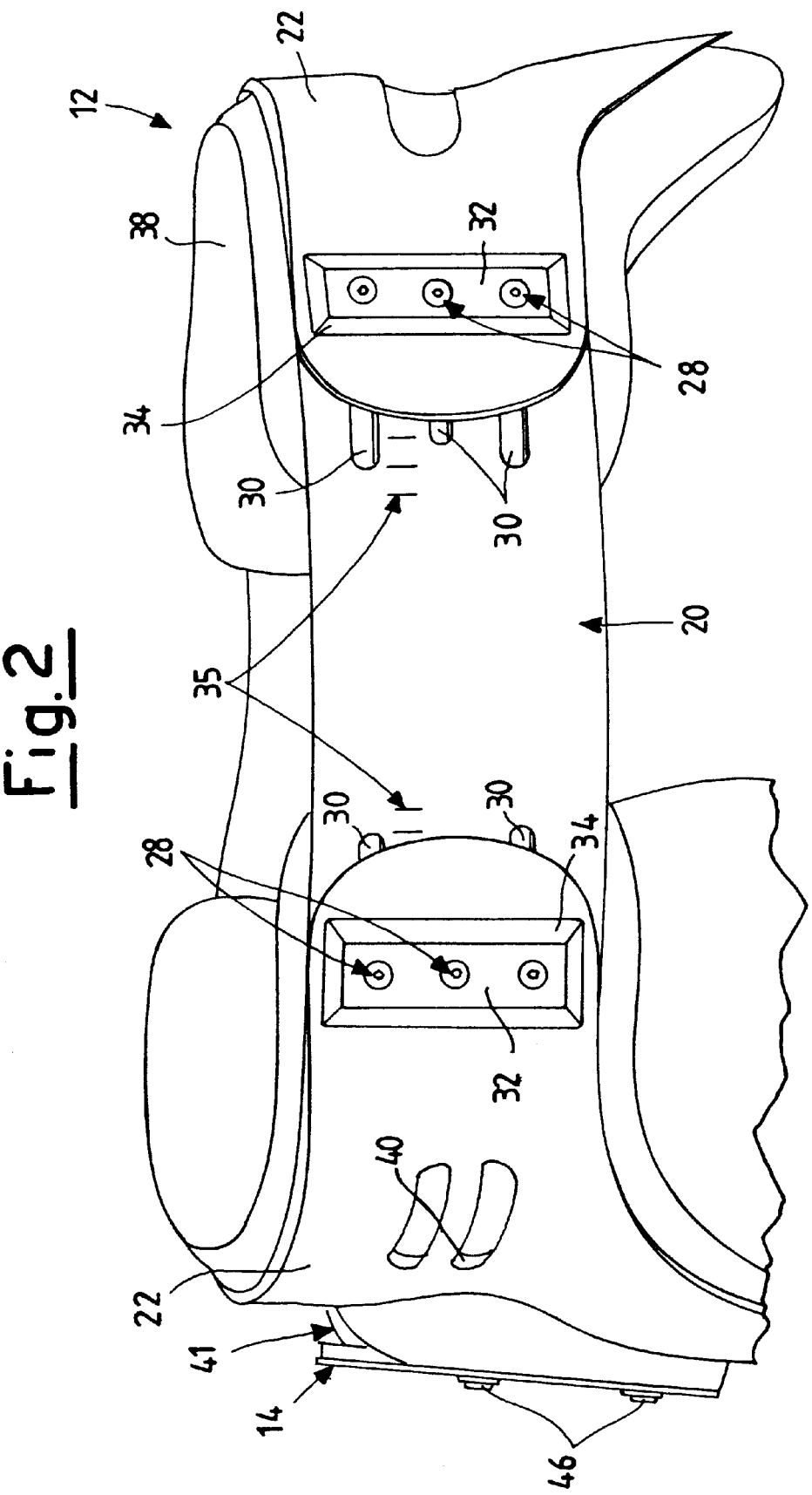
FIG. 2 is a rear elevation of a pelvis harness of the hip support according to the invention.
Figure 3:
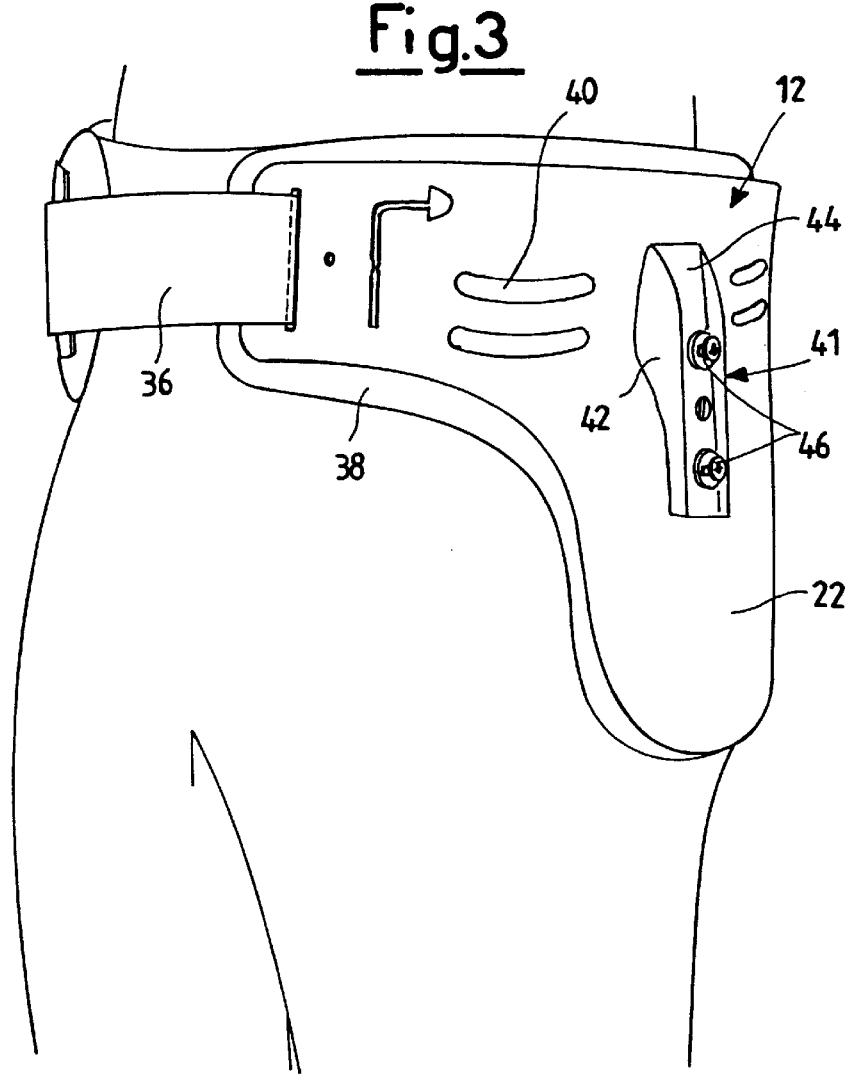
FIG. 3 is a perspective view of a detail of a pelvis harness of the hip support according to the invention.
Figure 4:
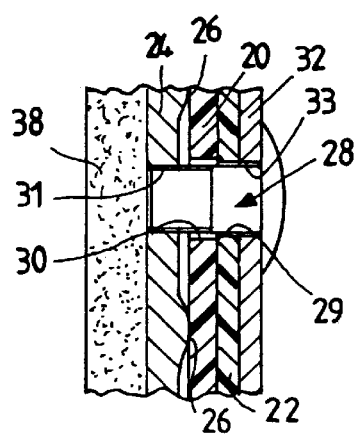
FIG. 4 illustrates a detail of a section taken at an orientable connection between a central belt and a containment element of the hip support according to the present invention.

With reference to the above figures, an improved hip support is illustrated and is designated, as a whole, by the reference number 11.

The hip support 11 is made up of a pelvic harness 12 which is connected, via an articulated rod 14, to a thigh harness 18.

The pelvis harness 12 is made up of a central belt 20 which carries, at each of its two ends, a containment element 22 for containing the head of the femur, the said containment element being connected by means of an orientable connection.

The connection is made by means of a plate 24 provided with rough parts in relief 26 facing the part of the central belt 20, which penetrate inside the body of the central belt 20 and fasten the connection. In particular, each of the two end portions of the central belt 20 overlaps one portion of each of the two containment elements 22 of the pelvis harness 12, keeping the containment elements 22 outwards with respect to the harness worn by a patient. The elements 22 are provided with three through holes 29 which are set so that they correspond to three transverse slots 30 of the belt 20 and, in addition, are aligned with three threaded holes 31 of each plate 24, which is set against the belt 20 with the rough parts 26 inserted in the body of the latter. On the opposite side, against the containment element 22, is set a further plate 32, which is also provided with three through holes 33 aligned with the holes 29. In the aligned holes 29, 33 and in the slots 30 is inserted a screw 28, as closing element that can be removed, which is blocked in the threaded hole 31. The plates 32 are designed to distribute the stresses caused by the screws 28 over a broad surface. Each plate 32 is housed in a seat of the element 22 that is identified by a border in relief 34.

In addition, on the central belt 20, and preferably set between two of the three slots 30, there are provided regulation notches. The notches 35 may be numbered or not and enable positioning of the elements 22 in an appropriate way, keeping the belt 20 always centered and thereby preventing the belt 20 from causing any discomfort to the patient.

Each of the containment elements 22 has, at an end opposite to the one connected to the central belt 20, a slit in which a belt 36 is inserted as closing element of the pelvis harness 12 when the latter is worn by a patient.

Fixed inside the pelvis harness is a lining 38 made of sponge material, which enables cushioning of contact between the patient's body and the rigid structure of the pelvis harness 12.

In addition, made in the containment elements 22 are through holes or recesses 40 for lightening the structure.

Each containment element 22 has a seat 41 in which one end of the articulated rod 14 is housed and blocked. The opposite end of the rod 14 is housed and blocked in a further seat 59 of the thigh harness 18.

The seat 41 of each containment element 22 is made by means of a thickened portion 42 provided with a longitudinal groove 44 in which are moreover made two threaded blind holes where screws 46 can be blocked. The screws 46 are each inserted in a slot 48 of a first portion of the articulated rod 14 and block it also with interposition of a washer.

The first portion of the rod 14 carries at one of its ends a hinge 50, of a type in itself known, the axis of which is substantially orthogonal to the containment element 22, and the maximum rotation of which can be limited. This is possible because a series of threaded holes are made along the perimeter of the hinge. In two of the holes a screw is inserted which forms a detent for an intermediate element 52 of the rod 14, and thus identifies the maximum rotation possible between the first portion and a second portion that is integral with the intermediate element 52.

The second portion of the rod 14 may be inclined to a greater or lesser extend towards the leg of the patient, since the ends of the rod, which are connected together, identify an orientable and clampable element. This element is made up of two orientable elements which have knurled front surfaces that are kept in contact with one another by a screw. These elements are in themselves known, and hence are not described any further herein.

The second portion of the rod 14 is fixed to the thigh harness 18 by means of a connection similar to that with which it is fixed to the pelvis harness 12.

The thigh harness 18 basically includes a tubular element which is shaped and open at the front. Along each of the two edges close to the opening, two slits are made in which two straps 54 are inserted as elements for closing the thigh harness in such a way that the harness embraces the thigh of a patient who is wearing the hip support 11 according to the invention.

The thigh harness 18 has a thickened portion 56 provided with a longitudinal groove 58 which constitutes the seat 59 for the second portion of the rod 14. The seat 59, identified by the groove 58, is aligned with the seat 41 of the first portion of the rod 14 identified by the groove 44. Of course, also in the groove 58 there are present two threaded blind holes, in each of which a screw 60 is blocked. The screws 60 are inserted, in slots 62 of the second portion of the rod 14, with interposition of a washer so as to make the connection between the rod 14, and the thigh harness 18.

Both the pelvis harness 12 and the thigh harness 18 of the hip support 11 are made by injection moulding. This makes it possible to obtain both the thigh harness and the pelvis harness with variable thicknesses so as to make the portions that are subject to higher stresses with a greater thickness, as well as, for example, making the borders in relief along the edges of their ends.

The improved hip support according to the present invention may be worn and adjusted as indicated in what follows.

First of all, the pelvis harness 12 is put on, causing the containment elements 22 to rotate and translate in order to adapt to the patient's body.

The adjustment can be carried out simply by loosening the screws in such a way as to separate the plate 24 from the central belt. At this point it is sufficient to bring the containment elements 22 into position so that they are correctly oriented, taking as reference the notches 35 and re-clamping the connection by tightening the screws 28.

Once adjusted, the pelvis harness can be closed by means of the strap 36.

Now, the thigh harness 18 is put on and is connected to the pelvis harness 12 by means of the rod 14, after inserting the screws, for limitation of rotation in the appropriate holes. Next, the element 53 is tightened, and then the thigh harness 18 is closed by tightening the straps 54.

It has in practice been found that an improved hip support according to the present invention is particularly advantageous because it is easily and quickly adaptable to the patient's body. This renders use of the hip support very flexible, and in particular adaptable to persons of very different build. In particular, the hip support according to the present invention is suited for being used by persons of small stature because, even when the orthopaedic technician is forced to cut the connection rod between the pelvis harness and the thigh harness, the alignment between the said elements is guaranteed even so by the seats 41, 59 in which the articulated rod 14 is inserted.

An improved hip support thus conceived may be subject to numerous modifications and variations, all of which do not depart from the scope of the invention. In addition, all the items can be replaced by elements that are technically equivalent.

In practice the materials used, as well as the dimensions, may be any whatsoever according to the particular technical requirements.

What is claimed is:

1. An improved hip support comprising at least one pelvis harness connected by means of an articulated rod to a thigh harness, said pelvis harness comprising at least one central belt with a first end and a second end adapted to carry at least one containment element of the head of a femur, said containment element being connected by means of an orientable connection, and being closeable by means of closing elements, wherein said orientable connection comprises at least one first plate, provided with rough parts in relief facing portions of said central belt and penetrating inside the body of the central belt, which are clamped together by means of closing elements that can be dismantled, said first plate having rough parts in relief that penetrate inside the body of said pelvis harness so as to clamp a coupling.

2. A hip support according to claim 1, wherein said first plate and said containment element are provided with aligned holes, in each of which a screw passes as a removable closing element, said screws being inserted in transverse slots on said central belt for clamping the coupling.

3. A hip support according to claim 2, wherein said pelvis harness comprises said central belt on top of which are set said containment elements, and on a side opposite to the one where said containment elements overlap, said first plates which have said rough parts in relief that are inserted in the body of said central belt, said parts being fixed by means of said screws.

4. A hip support according to claim 2, wherein said coupling includes a second plate, said second plate provided with through holes which are aligned with said through holes of said first plate and of said containment element, said second plate being associated to the same containment element on the outer part of the latter, so as distribute the stresses caused by said screws over a substantially broad surface.

5. A hip support according to claim 4, wherein each of said second plates is housed in a seat made in said containment element.

6. A hip support according to claim 1, wherein each of said containment elements has, at its end opposite to the one connected to said central belt, a closing element of said pelvis harness which consists of at least one slit in which is inserted at least one strap which constitutes said closing element of said pelvis harness.

7. A hip support according to claim 1, wherein inside said pelvis harness is fixed a lining that enables cushioning of the contact between the patient's body and the rigid structure of said pelvis harness.

8. A hip support according to claim 1, wherein each containment element has a seat in which one end of said articulated rod is housed and blocked in position.

9. A hip support according to claim 8, wherein said seat for each containment element is made by means of at least one thickened portion provided with at least one groove in which threaded holes are made where screws can be blocked, each of said screws being inserted in slots made in a first portion of said articulated rod.

10. A hip support according to claim 1, wherein said thigh harness is substantially made by means of a shaped tubular element provided with a longitudinal opening, along each of two edges close to said opening there being made slits in which elements are inserted for closing said thigh harness, so as to embrace the thigh of a patient who is wearing said hip support, said thigh harness moreover having a seat for a second portion of said articulated rod.

11. A hip support according to claim 10 wherein said seat of said thigh harness is identified by a thickened portion provided with a second groove, said second groove having threaded holes, in each of which a screw is blocked, said screws being inserted in slots of said second portion of said articulated rod.

12. A hip support according to claim 1, wherein said pelvis harness and said thigh harness are made by injection-molding.

13. A hip support according to claim 1, wherein said containment elements of said pelvis harness have through holes or recesses for lightening the structure.

14. A hip support according to claim 1, wherein on said central belt, adjustment notches are provided, said notches enabling said containment elements to be positioned appropriately, maintaining said central belt always centered thereby preventing said central belt from causing discomfort to the patient.

* * * * *